United States Patent [19]

Charbonneau et al.

[11] Patent Number: 5,391,374
[45] Date of Patent: Feb. 21, 1995

[54] FRAGRANCE DELIVERY COMPOSITIONS HAVING LOW AMOUNTS OF VOLATILE ORGANIC COMPOUNDS

[75] Inventors: Jack W. Charbonneau, Somerset, Wis.; Daniel B. Pendergrass, Jr., Mendota Heights, Minn.

[73] Assignee: Minnesota Mining and Manufacturing Company, St. Paul, Minn.

[21] Appl. No.: 59,500

[22] Filed: May 10, 1993

[51] Int. Cl.⁶ .................. A61K 7/00; A61K 7/035
[52] U.S. Cl. .................. 424/401; 424/63; 424/69; 424/489; 512/4
[58] Field of Search .......... 424/401, 63, 69, 489; 512/4

[56] References Cited

U.S. PATENT DOCUMENTS

| | | | |
|---|---|---|---|
| 3,640,629 | 2/1972 | Geiser | 401/132 |
| 4,751,934 | 6/1988 | Moir et al. | 132/79 |
| 4,756,906 | 7/1988 | Sweeny | 424/63 |
| 4,879,174 | 11/1989 | Marabella | 428/321 |
| 4,952,400 | 8/1990 | Tararuj et al. | 424/401 |
| 4,988,557 | 1/1991 | Charbonneau | 428/204 |
| 5,000,947 | 3/1991 | Nichols | 424/69 |
| 5,043,161 | 8/1991 | Scarpelli et al. | 424/63 |
| 5,223,251 | 6/1993 | Nichols | 424/69 |

OTHER PUBLICATIONS

Jackson, E. M., PhD, *The Toxicologist's Report*, vol. 108, pp. 47–48, "Encapsulation and its Toxicological Implications", Apr. 1993.

Flick, E. W., *Cosmetic and Toiletry Formulations*, (1984), Noyes Publications, New Jersey, pp. 96–103, 105, 106, 110, 111, 241, 242, 243, 594, 595.

*Primary Examiner*—D. Gabrielle Phelan
*Assistant Examiner*—Amy L. Hulina
*Attorney, Agent, or Firm*—Gary L. Griswold; Walter N. Kirn; Dale A. Bjorkman

[57] ABSTRACT

A fragrance-delivery composition is provided having cake-forming components and microcapsules containing fragrance oil. The composition is a coherent cake, and has a VOC content less than 250 grams of per liter less water, fragrance oil and exempt solvents.

18 Claims, No Drawings

FRAGRANCE DELIVERY COMPOSITIONS HAVING LOW AMOUNTS OF VOLATILE ORGANIC COMPOUNDS

FIELD OF THE INVENTION

The present invention relates to fragrance-containing compositions. More specifically, the present invention relates to compositions for delivery of a fragrance wherein the composition comprises a small amount of volatile organic compounds.

BACKGROUND OF THE INVENTION

Fragrance-containing compositions have long been utilized to provide a pleasing odor associated with an individual as an aspect of their personal hygiene, or to provide a fragrance in an enclosed environment. Such compositions are typically used either to mask an unpleasant odor or to provide a specific aesthetic sensation that may be associated with certain smells. A primary example of the use of a fragrance is in the so called "fine fragrance" industry, which provides perfumes, colognes and the like for use on the human body.

U.S. Pat. No. 3,640,629 to Geiser discloses a perfumed dispenser comprising a tape or strip of narrow sheet material having a raised portion at each end and pressure rupturable microcapsules containing aroma chemical entrapped in the trough formed between the raised edges. The perfume containing microcapsules are free flowing in the dispenser.

U.S. Pat. No. 4,751,934 to Moir et al. discloses a cosmetic sampler formed by screen printing a slurry of cosmetic powder and solvent onto a paper base. This sampler is identified as providing unit doses or single applications of creams, lipsticks, fragrances, pharmaceuticals, lotions, and other high viscosity, waxy materials. See the abstract.

U.S. Pat. No. 4,756,906 to Sweeney discloses cosmetic compositions that have modifiable color characteristics. The composition contains a first pigment and microcapsules containing a second pigment. Upon rupture of the microcapsules, the coloration of the Second pigment is added to the composition, altering its color characteristics. Options for the selection of the microcapsule fill material are listed at column 7, lines 10-16, and include fragrance oils.

U.S. Pat. No. 4,879,174 to Marabella discloses a device for exposing colorant to be transferred, wherein microcapsules having colorant on their exterior surfaces can transfer the colorant when the capsules contain liquid which wet the colorant. The liquid contained within the microcapsule may optionally be any liquid capable of wetting the colorant sufficiently to carry it off the surface of the substrate to which the capsules are bound, including fragrance oils. See col. 3, lines 54–69.

SUMMARY OF THE INVENTION

Due to the growing concern about the emission of organic compounds that may have an adverse impact on the environment, it is now desirable to eliminate or limit the use of non-essential organic compounds from all compositions. Until now, it was thought that a carrier solvent was essential for the effective delivery of fragrance-containing compositions intended for the routine every-day use by consumers. Carrier solvents act to dilute the often very potent fragrance liquids. Consumers have come to expect that they must apply a certain minimum amount of liquid to the skin in order to achieve a noticeable olfactory sensation. A fragrance-containing composition that has a significantly higher concentration of fragrance, i.e. has less carrier solvent, would not be accepted by the marketplace because it would be viewed as "too strong."

The present invention provides a fragrance delivery composition consisting essentially of cake-forming components and microcapsules containing fragrance oil. The composition is in the form of a coherent cake, wherein the majority of the microcapsules may be removed from the cake without breakage of the microcapsules. A coherent cake is defined as a multiple application reservoir of fragrance-containing material that has a internal cohesion sufficient to hold the material together without breakage of the cake when a sample having the dimensions of at least 0.12 cm by 2 cm by 2 cm is inverted. The composition has a VOC content less than 250 grams of per liter less water, fragrance oil and exempt solvents. The composition may also optionally include colorants wherein the colorants are selected such that the composition presents a uniform color as applied to the skin and following rupture of some or all microcapsules.

DETAILED DESCRIPTION OF THE INVENTION

The present invention provides a fragrance delivery composition that is substantially free of carrier solvent. Because there is substantially no alcohol or other solvent and the cake itself is coherent, the present composition is "spill free" in the sense that there will be no solvent flow and damage to, e.g. a purse or luggage, by breakage or accidental opening of the package containing the fragrance. Because the present compositions do not contain a large amount of solvent, the fragrance may be applied to the skin without incurring a drying effect as would be experienced by, for example, an alcohol carrier solvent.

The present composition delivers fragrance in a highly controlled manner through finger or wand application, so the amount of fragrance delivered may be well regulated by the user. When the composition contains a colorant, an enhanced visual feedback of amount that is on the finger or wand applicator is provided. Additionally, the present compositions do not suffer the disadvantage of fragrance-containing compositions that are sprayed on the skin, wherein stray drops of liquid may land on clothing and oil stain or otherwise damage fabrics.

Delivery of fragrance through a coherent cake using encapsulation technology has a number of advantages over waxy compositions having fragrance embedded therein, such as those disclosed in Flick, "Cosmetic and Toiletry Formulations," Noyes Publications, Park Ridge, N.J. 1984. Because the fragrance is trapped within the microcapsule, all of the notes, including the highly volatile top notes, are effectively contained within the composition and are not lost before application to the user. Additionally, a coherent cake offers a good texture and appealing velvety feel to the user, while waxes or lotions tend to impart a tacky, sticky or slippery feel. The user may also find the removal of a single application of fragrance from a wax difficult as compared to that of the present coherent cake.

For purposes of the present invention, a volatile organic compound (VOC) is any volatile organic material having a vapor pressure at 20° C. greater than 0.1 Torr (mm Hg). More preferably, Volatile Organic Compounds may be defined as having a vapor pressure at 20° C greater than 0.02 Torr. Expressly excluded from this definition are fragrance oils (the intended product to be delivered to the consumer) and "exempt solvents." A fragrance oil for purposes of the present invention is a substance or complex mixture of aroma chemicals, natural essential oils, and other functional components, the sole purpose of which is to impart an odor or scent, or to counteract a malodor. Exempt solvents for purposes of the present invention are methane, carbon monoxide, carbon dioxide, carbonic acid, metallic carbides or carbonates, ammonium carbonate, 1,1,1-trichloroethane, methylene chloride, trifluoromethane (FC-23), trichlorotrifluoroethane (CFC-113), dichlorodifluoromethane (CFC12), trichlorofluoromethane (CFC-11), chlorodifluoromethane (CFC-22), dichlorotetrafluoroethane (CFC-114), and chloropentafluoroethane (CFC-115).

The measurement of VOC content is in the units of grams of volatile organic material per liter less water, fragrance oil and exempt solvents. This measurement is calculated according to the following formula:

$$VOC(g/L) = \frac{\text{wt of } VC(g) - \text{wt water}(g) - \text{wt fragrance oil}(g) - \text{wt exempt solvents}(g)}{\text{vol total}(l) - \text{vol water}(l) - \text{vol fragrance oil}(l) - \text{vol exempt solvents}(l)}$$

wherein, wt of $VC(g)$ is the total weight of volatile compounds in grams, wt water(g) is the weight of water in the material in grams, wt fragrance oil(g) is the weight of fragrance oil in grams, wt exempt solvents(g) is the weight of exempt solvents in grams, vol total(1) is the total volume of the material in liters, vol water(1) is the volume of water in liters, vol fragrance oil(1) is the volume of fragrance oil in liters and, vol exempt solvents(l) is the volume of exempt solvents in liters.

As noted above, the coherent cake of the present invention will not fall apart when a container containing the cake is inverted. In an alternative manner of measuring the coherent nature of the cake, a hardness test measured using a Shore A hardness measurement device may be performed in accordance with ASTM D 2240-86. Preferably, the Shore A hardness has a minimum value of about 1.2 Newtons. If the cake has a Shore A hardness measurement value less than this it may not withstand expected sudden movements (such as being dropped) that may occur in transit of the product. Cakes that fall apart during ordinary transit would not be considered to be spill free. More preferably, the Shore A hardness is at least about 1.8 Newtons. When a dose of the composition is to be removed by contact with the finger, the cake preferably is not so hard that light finger pressure will not remove any of the material of the cake. When the perfume composition is to be applied using a wand or an applicator brush, greater hardness of the cake will be acceptable. In all cases, the cake must be soft enough to be able to remove material from the cake under normal application conditions without excessive rupture of the microcapsules. In other words, the majority of the microcapsules should survive removal from the cake so that they can be applied to the skin intact and ruptured thereon.

Cakes of the present invention are preferably at least 0.1 cm thick, and more preferably at least 1.5 cm thick. The cake may be provided in any shape, such as circular, oval, rectangular and so on. For convenient finger application, the length and width of the cake are at least about 1.5 cm, and more preferably at least 2 cm. Multiple fragrance-containing compositions may optionally be provided from the same container in a side-by-side fashion, such as presently available for eye-shadow compositions.

Microcapsules useful in the present invention may be made by a wide variety of processes. These varied processes provide different techniques for producing capsules of varying sizes, alternative materials for the composition of the capsule shell and various materials within the shell. Some of these various processes are shown in U.S. Pat. Nos. 3,516,846; 3,516,941; 3,778,383; 4,087,376; 4,089,802; 4,100,103 and 4,251,386 and British Pat. Specification Nos. 1,156,725; 2,041,319 and 2,048,206. A wide variety of different materials may also be used in making the capsule shells. Popular materials for shell formation are the polymerization reaction products between urea and formaldehyde or melamine and formaldehyde, or the polycondensation products of monomeric or oligomeric polymers of dimethylolurea or methylolated urea with aldehydes. A variety of capsule forming materials are disclosed, for example, in U.S. Pat. Nos. 3,516,846 and 4,087,376 and U.K. Patent Specification Nos. 2,006,709 and 2,062,570. Preferred microcapsules may be found in Matson, U.S. Pat. No. 3,576,941, in particular, Example 20.

The cake-forming components of the present invention comprise particles and liquid or semi-solid materials that provide agglomeration of the microcapsules and other components of the composition to render the resultant composition cohesive and at least somewhat firm. Examples of such cake-forming components include particles such as silica, talc, pearlescent powders (e.g., mica particles or surface treated mica particles such as encapsulated titanated mica); and liquids or semi solids such as metal carboxylates e.g., zinc stearate), natural or synthetic waxes (e.g., beeswax, carnauba wax, micronized polyethylene waxes), lipids, fatty alcohols; and mixtures thereof. Pearlescent powders are particularly advantageous for use as cake-forming components because they additionally impart color to the composition.

Additional components may be present in the compositions that are conventional in cosmetic cake compositions, provided that they do not interfere with the function of the inventive compositions as defined herein. Examples of such non-interfering components include preservatives, stabilizers, antimicrobials, vitamins and the like. Free fragrance oil may be provided in the cake composition, in addition to the encapsulated fragrance oil. Addition of free fragrance oil provides a perceptible fragrance to the cake without the need to rupture microcapsules.

Colorants may also be incorporated in the present compositions, provided that such materials do not result in a differential color where there are unbroken fragrance-containing capsules as compared to where there are broken capsules. Such a color differentiation is considered to be undesirable because it could result in an uneven coloration of the region of application of fragrance. For the present fragrance delivery compositions, it is desirable to have only a modest color signature, if any at all, at the location for application of the fragrance on the body of the user. Careful selection of the colorant can provide visibility of the removed material on the finger or applicator wand, while becoming substantially invisible when applied to the skin.

Both organic and inorganic pigments may be used in the practice of the present invention. Examples of such pigments include chrome green, iron oxides, aluminum powder, bismuth citrate, bismuth oxychloride, bronze powder, copper powder, disodium EDTA-copper, ferric ammonium ferrocyanide, ferric ferrocyanide, lead acetate, manganese violet, potassium sodium copper, chlorophyllin (chloro-phyllin-copper complex), zinc oxide, aluminum hydroxide, aluminum stearate, barium sulfate, magnesium aluminum silicate, magnesium carbonate, magnesium oxide, magnesium stearate, magnesium trisilicate, tin oxide, zinc carbonate, zinc stearate and the like. In addition to pure pigment, cosmetic lakes may also be used. Lakes are commercially available water insoluble pigments that comprise soluble dyes on inorganic substrates. Dyes also may be incorporated into the present composition. Preferred dyes are those presently approved for use in cosmetic compositions, thereby avoiding the expensive and time-consuming process of obtaining government approval for use of new materials on the skin.

The above described coherent cake compositions are formulated in a manner routine in the cosmetic art for making coherent cakes, with the specific proviso that care must be taken in the mixing and any heating or other handling steps to avoid undesirable levels of breakage of the microcapsules containing fragrance. Thus, vigorous stirring, compaction and the like may not be appropriate when incorporating particularly fragile capsules. One may, for example, utilize known formulations for pressed powder eyeshadows available in the literature (such as described in Flick, "Cosmetic and Toiletry Formulations," Noyes Publications, Park Ridge, N.J. 1984), substituting some of the talc or certain pigments of the eye shadow formulations with fragrance-containing microcapsules to provide new fragrance delivery compositions.

When the cake-forming component is a particle material, it is possible to significantly reduce the amount of microcapsules used in the composition because the particle material both provides significant structure and body to the cake and also acts as a filler. When the cake-forming component is a liquid or semi-solid material, a larger portion of the cake must be microcapsules in order to provide the structure and body to the cake. Preferably, the coherent cake is formulated using a blend of different types of cake-forming components, i.e. a blend of particles and liquid or semi-solid materials. Especially preferred compositions consist essentially of
 a) 10–50% microencapsulated fragrance oil,
 b) 30–90% cake-forming components that are particle materials, and
 c) 0–20% cake-forming components that are liquid or semi-solid materials.

Particularly preferred compositions consist essentially of
 a) 20–40% microencapsulated fragrance oil,
 b) 20–60% talc
 c) 10–40% pearlescent pigment, and
 d) 0.05–2% preservative.

The following examples are provided for illustrative purposes only, and are not intended to limit the invention. All of the fragrance-containing capsules used herein contain fragrance encapsulated in accordance with U.S. Pat. No. 3,576,941, Example 20. These capsules have a nominal mean diameter of 20 microns.

Examples 1–3 illustrate the ability to add components any time in the cake-making process to modify the firmness and texture characteristics of the composition.

EXAMPLE 1

A fragrance-containing coherent cake was prepared by first blending 3.64 Flamenco Superpearl powder, commercially available from the Mearl Corporation, NY, with 6.36 g fragrance-containing microcapsules.

This premixed blend was mixed with 5 g petrolatum and 2 g isopropylpalmitate (IPP). The resulting formulation was packed into 1" diameter tins.

EXAMPLE 2

A coherent cake was prepared comprising 10 g of the premixed blend of Example 1 above and 1 g of tetradecanol, which was mixed with sufficient $CH_2Cl_2$ to form a smooth paste, warmed to distribute and drive off the solvent and warm pressed into a silver pillbox.

EXAMPLE 3

A composition was prepared comprising 10 g of the premixed blend of Example 1 above with 0.5 g tetradecanol and 0.2 g IPP. This Composition was heated to help distribute the components and was warm pressed into a pillbox.

The coherent cake of Example 3 was firmer than that of the previous examples, and delivered product more smoothly as well.

Coherent cakes of fragrance-containing delivery were prepared through first preparing "master batches" of microencapsulated fragrance, and then further formulating to provide the desired cake. Examples described below utilized the following master batches.

| Master Batch A | |
| --- | --- |
| talc | 35 |
| ZN stearate | 9 |
| magnesium carbonate | 1 |
| Flamenco Superpearl ™ pigment | 20 |
| sorbitol | 0.84 |
| microcapsules | 34.16 |
| $H_2O$ | 9 |
| Master Batch B | |
| | parts |
| talc | 50 |
| Flamenco Superpearl ™ pigment | 15 |
| microcapsules | 20 B" |

The compositions of Examples 4–18 were mixed by stirring, and packed into one inch diameter circular tin pillboxes.

EXAMPLE 4
5 g "Master Batch B"
0.15 g Tween ™ 20 (available from ICI Americas, Wilmington, Del.
2 g IPP
0.1 g sorbitol
1 g $H_2O$

EXAMPLE 5

5 g "Master Batch B"

2 g IPP
1 g H$_2$O
0.15 g Tween ™ 20
0.15 g sorbitol

EXAMPLE 6

5 g "Master Batch A"
3.5 g IPP

EXAMPLE 7

5 g "Master Batch B"
2.25 g IPP

EXAMPLE 8

5 g ""Master Batch A"
2 g IPP

EXAMPLE 9

5 g "Master Batch A"
0.75 g ACumist ™ micronized polyethylene wax
3.5 g IPP
(ACumist ™ micronized polyethylene wax commercially available from Allied-Signal Inc. Columbia Rd. Morristown, N.J. 07960.)

EXAMPLE 10

5 g "Master Batch A"
1 g glycerol
3 g IPP
1 g H$_2$O
1 g ACumist ™
0.18 g Tween ™ 20

EXAMPLE 11

5 g "Master Batch B"
1 g glycerol
3 g IPP
1 g H$_2$O
1 g ACumist ™
0.18 g Tween ™ 20

EXAMPLE 12

5 g "Master Batch A"
3 g petrolatum
1.5 g IPP
0.5 g H$_2$O
0.15 g Tween ™ 20

EXAMPLE 13

5 g "Master Batch A"
1 g petrolatum
0.5 g IPP
0.2 g H$_2$O
0.06 Tween ™ 20

EXAMPLE 14

5 g "Master Batch A"
2 g petrolatum
1 g IPP
0.4 g H$_2$O
0.12 g Tween ™ 20

EXAMPLE 15

5 g "Master Batch A"
0.66 g glycerol
2 g IPP
0.66 g ACumist ™
0.12 g Tween ™ 20

EXAMPLE 16

5 g "Master Batch A"
0.33 g glycerol
1 g IPP
0.33 ACumist ™
0.06 g Tween ™ 20

EXAMPLE 17

5 g "Master Batch B"
0.66 g glycerol
2 g IPP
0.66 ACumist ™
0.12 g Tween ™ 20

EXAMPLE 18

5 g "Master Batch B"
0.33 g glycerol
1 g IPP
0.33 g ACumist ™
0.06 g Tween ™ 20

EXAMPLE 19

8.82 g fragrance-containing microcapsules
3.39 g mineral oil caps
1.13 g Gold 220 C Flamenco ™ pigment
1.65 g tetradecanol A mixture of hexanes and isopropanol was combined with tetradecanol under mild heating to a somewhat wet cake consistency. This composition was packed in ointment tins and dried to remove the solvents.

EXAMPLE 20

8.82 g microcapsules
3.39 g Flamenco Superpearl ™ pigment
1.30 g mineral oil
1.5 g tetradecanol
This composition was processed as above.

EXAMPLE 21

5.29 g microcapsules
6.97 g mineral oil microcapsules, nominal 20 micron diameter
1.16 g Gold 220c Flamenco ™ pigment
1.58 g tetradecanol
This composition was processed as above.

Both Examples 19 and 21 have very little sparkle in the tin or on skin, but provide a gold hue on transfer of the composition to the finger tip.

EXAMPLE 22

115.8 g microcapsules containing fragrance oil 66 g Flamenco Superpearl ™ pigment, and 20.7 g tetradecanol, were mixed with 250 ml hexanes in a glass cake tray to distribute the tetradecanol. When the hexanes evaporated, the slight crust was broken up and mixed in before attempting to pack the powder. It did not form a good cake, so 60 ml of hexanes was added to 150 g of the powder before packing into 7 ml ointment tins. The samples were allowed to dry overnight. A crust formed again and the underlying material was a little too soft. Eight drops of a 10% sorbitol/water solution was added to each container and allowed to dry. Enough isopropanol was then added to each container to moisten the cake and the surface was rubbed smooth. This seemed to carry some of the tetradecanol back into the cake. When the samples dried overnight there was still a thin crust of firmer material which was scraped off.

EXAMPLE 23

A batch with 49.5 g Flamenco Superpearl ™ pigment, 13.65 g tetradecanol, and 86.85 g microcapsules containing fragrance oil was prepared by adding the tetradecanol in 60 ml hexanes to the mixed capsules/pigment. The damp powder packed easily into the tins. After drying overnight, the crust was "washed" back into the cake with isopropanol as before. The remaining crust was scraped off.

EXAMPLE 24

Perfume compositions with a gold pearlescent pigment were prepared as follows:
The preparations were:
5 parts tetradecanol (In $CH_2Cl_2$)
50 parts Cloisomme Gold 222C (The Mearl Corp. New York) pigment
87.5 parts microcapsules containing fragrance oil
A small amount of isopropanol and 10% sorbitol solution (about 6–8 drops per 4 grams) was added to help provide firmness to the composition.

One sample was packed in a silver pill box as described above. Another was packed in half of an eyeshadow compact side by side with another coherent cake formulated using a different fragrance oil. The two-fragrance compact was provided with two applicators.

EXAMPLE 25

A coherant cake was prepared by mixing 29.25 parts Supratino ™ talc (commercially available from Cypress Foote Mineral Company, Malvern, Pa.) with 30 parts Flamenco Velvet ™ and 10 parts Cloisonne ™ Gold 222C pigments (both commercially available from The Mearl Corporation, New York). Thirty parts of microencapsulated fragrance was added to this mixture, followed by addition of 0.30 parts Germale II ™ preservative (commercially available from Sutton Laboratories, Chatham, N.J.), 0.30 parts methylparben and 0.10 parts propylparaben. The resultant material was pressed onto a 2.75 cm by 2.75 cm compact that was 0.36 cm deep.

We claim:

1. A fragrance delivery coherent cake consisting essentially of cakeforming components and microcapsules containing fragrance oil, said cake having a Shore A hardness value of at least about 1.2 Newtons, wherein the majority of the microcapsules may be removed from the cake by light finger pressure without breakage of the microcapsules, and wherein said fragrance delivery cake has a VOC content less than 250 grams per liter less water, fragrance oil and exempt solvents, and wherein the cake is at least 0.1 cm thick.

2. The coherent cake of claim 1, wherein said cake has a VOC content less than 100 grams per liter less water, fragrance oil and exempt solvents.

3. The coherent cake of claim 1, wherein said cake contains no Volatile Organic Compounds.

4. The coherent cake of claim 1, wherein said cake is substantially free of unencapsulated fragrance oil.

5. The coherent cake of claim 1 wherein said cake having a Shore A hardness value of at least about 1.8 Newtons.

6. The coherent cake of claim 1, further consisting essentially of a colorant, such that the cake presents a uniform color as applied to the skin and following rupture of some or all capsules.

7. The coherent cake of claim 1, wherein the cake is at least 1.5 cm thick.

8. The coherent cake of claim 1, wherein the cake is provided in a generally circular or oval shape.

9. The coherent cake of claim 1, wherein the cake is provided in a generally rectangular shape.

10. The coherent cake of claim 8, wherein the length and width of the cake are each at least about 1.5 cm.

11. The coherent cake of claim 9, wherein the length and width of the cake are each at least about 1.5 cm.

12. The coherent cake of claim 8, wherein the length and width of the cake are each at least about 2 cm.

13. The coherent cake of claim 9, wherein the length and width of the cake are each at least about 2 cm.

14. The coherent cake of claim 1, consisting essentially of
a) 5–95% microencapsulated fragrance oil, and
b) 5–95% cake-forming components.

15. The coherent cake of claim 14, wherein said cake-forming components comprise a blend of particles and liquid or semi-solid materials.

16. The coherent cake of claim 14, consisting essentially of
a) 10–50% microencapsulated fragrance oil,
b) 30–90% cake-forming components that are particles materials, and
c) 0–20% cake-forming components that are liquid or semi-solid materials.

17. The coherent cake of claim 14, consisting essentially of
a) 20–40% microencapsulated fragrance oil,
b) 20–60% talc
c) 10–40% pearlescent pigment, and
d) 0–2% preservative.

18. The coherent cake of claim 1, provided in a cosmetic compact case.

* * * * *

UNITED STATES PATENT AND TRADEMARK OFFICE
CERTIFICATE OF CORRECTION

PATENT NO.: 5,391,374

DATED: February 21, 1995

INVENTOR(S): Jack W. Charbonneau and Daniel B. Pendergrass, Jr.

It is certified that error appears in the above-identified patent and that said Letters Patent is hereby corrected as shown below:

Column 6, Line 15, after "NY," insert --NY--. (PTO error)

Column 6, Line 62, after "DE" insert --)--. (PTO error)

Column 9, Line 48, delete "cakeforming" and insert --cake-forming-- therefore. (PTO error)

Column 10, Line 51, delete "0-2%" and insert --0.05-2%-- therefore. (PTO error)

Signed and Sealed this

Twenty-ninth Day of April, 1997

Attest:

BRUCE LEHMAN

Attesting Officer

Commissioner of Patents and Trademarks